United States Patent [19]

Cooper et al.

[11] Patent Number: 5,719,186
[45] Date of Patent: Feb. 17, 1998

[54] AMIDE DERIVATIVES AND THEIR THERAPEUTIC USE

[75] Inventors: Barrett Randoph Cooper, Durham; James Leroy Kelley; David Lee Musso, both of Raleigh; Jeffrey Leaman Selph, Durham, all of N.C.

[73] Assignee: Glaxo Wellcome Inc., Research Triangle Park, N.C.

[21] Appl. No.: 737,501

[22] PCT Filed: May 9, 1995

[86] PCT No.: PCT/GB95/01039

§ 371 Date: Nov. 8, 1996

§ 102(e) Date: Nov. 8, 1996

[87] PCT Pub. No.: WO95/30644

PCT Pub. Date: Nov. 16, 1995

[30] Foreign Application Priority Data

May 10, 1994 [EP] European Pat. Off. ............ 94303351

[51] Int. Cl.$^6$ .................... A61K 31/65; A61K 31/38; A61K 31/40; A61K 31/33

[52] U.S. Cl. .................... 514/617; 514/432; 514/456; 514/429; 514/408; 514/183; 564/180; 549/23; 549/398; 549/407; 548/570; 548/950

[58] Field of Search .................... 564/180; 514/617, 514/429, 408, 183, 432, 456; 548/570, 950; 549/23, 398, 407

[56] References Cited

U.S. PATENT DOCUMENTS

| | | | |
|---|---|---|---|
| 3,312,730 | 4/1967 | Winter et al. | 564/180 |
| 3,763,229 | 10/1973 | Noguchi et al. | 514/617 |
| 4,018,817 | 4/1977 | Noguchi et al. | 514/617 |
| 4,888,355 | 12/1989 | Clemence et al. | 514/429 |
| 5,071,875 | 12/1991 | Horn et al. | 514/613 |

FOREIGN PATENT DOCUMENTS

| | | |
|---|---|---|
| A92/12959 | 8/1992 | WIPO . |
| A94/26692 | 11/1994 | WIPO . |
| A94/26693 | 11/1994 | WIPO . |

OTHER PUBLICATIONS

Derwent Publications, Ltd., Database, 24 Mar. 1992.

Angelova I. et al., "Conversion of 5–aryl–3–phenyl–2, 4–pentadienoic acid and their amides into indan derivatives", Chemical Abstracts, 8 Jul. 1974, pp. 116–117.

*Primary Examiner*—Deborah Lambkin
*Attorney, Agent, or Firm*—Shah R. Makujina; Robert T. Hrubiec

[57] ABSTRACT

Novel carbocyclic amides together with their salts, solvates and physiologically active derivatives which have a number of uses in medicine, in particular as central muscle relaxants, and in the treatment or prophylaxis of anxiety, inflammation, arthritis and pain.

3 Claims, No Drawings

AMIDE DERIVATIVES AND THEIR THERAPEUTIC USE

This application is filed pursuant to 35 U.S.C. §371 as a United States National Phase Application of International Application No. PCT/US95/01039 filed 09 May 1955 which claims priority from EP 94303351.4 filed 10 May 1994.

The present invention relates to substituted carbocyclic amides, to pharmaceutical compositions containing them, to methods for their preparation and their use in therapy, in particular as muscle relaxants.

The major limiting side effects of many clinically effective muscle relaxants and anticonvulsants are the induction of sedation and incoordination in the recipient, which severely limits the usefulness of these compounds. Similar side effects have been found with drugs used in the treatment of anxiety, such as, benzodiazepines. Although these effects may be transient, patients on such therapy are often unable to drive or participate in certain occupations.

We have now found novel carbocyclic amides which have muscle relaxant activity but with less of the sedation and incoordination side-effects observed with known muscle relaxants.

Accordingly, the present invention provides the following novel compounds:

(E)-2-(4-Chloro-1-indanylidene)acetamide
(E)-2-(4-Methyl-1-indanylidene)acetamide
(E)-1-(2-(6-Fluoro-1-indanylidene)acetyl)pyrrolidine
(E)-2-(6-Fluoro-1-indanylidene)-N-phenylacetamide
(E)-1-(2-(6-Fluoro-1-indanylidene)acetyl)azetidine
(E)-2-(6-Fluoro-1-indanylidene)-N-methoxy-N-methylacetamide
(Z)-2-(6-Fluoro-2-nitrooxy-1-indanylidene)acetamide
(E)-2-(6-Fluoro-1-indanylidene)-N-(2-hydroxyethyl)acetamide
(Z)-2-(6-Fluoro-2-methoxy-1-indanylidene)acetamide
(Z)-2-(2,3-Dibromo-6-fluoro-1-indanylidene)acetamide
(E)-2-(6-Fluoro-1-indanylidene)thioacetamide
(E)-N-Cyclopentyl-2-(6-fluoro-1-indanylidene)acetamide
(Z)-2-(2-Acetoxy-6-fluoro-1-indanylidene)acetamide
(Z)-2-(2-Bromo-6-fluoro-1-indanylidene)acetamide
(E)-2-(4,6-Difluoro-1-indanylidene)-N-(2-hydroxyethyl)acetamide
(E)-N-Cyclopropyl-2-(7-methyl-1-indanylidene)acetamide
(E)-2-(6-Cyano-1-indanylidene)acetamide
(Z)-2-(2-Bromo-4,6-difluoro-1-indanylidene)acetamide
(E)-2-(6-Bromo-1-indanylidene)-N-cyclopropylacetamide
(E)-2-(6-Bromo-1-indanylidene)-N-methylacetamide
(E)-2-(6-Methoxy-1-indanylidene)acetamide
(E)-2-(7-Chloro-1,2,3,4-tetrahydro-1-naphthylidene)-N-cyclopropylacetamide
(E)-2-(5-Bromo-1,2,3,4-tetrahydro-1-naphthylidene)-N-cyclopropylacetamide
(E)-N-Cyclopropyl-2-(1,2,3,4-tetrahydro-7-methoxy-1-naphthylidene)acetamide
(E)-N-Cyclopentyl-2-(7-fluoro-1,2,3,4-tetrahydro-1-naphthylidene)acetamide
(E)-N-Cyclopropyl-2-(1,2,3,4-tetrahydro-6-methoxy-1-naphthylidene)acetamide
(E)-N-Benzyl-2-(7-fluoro-1,2,3,4-tetrahydro-1-naphthylidene)acetamide
(E)-N-Cyclopropyl-2-(5-fluoro-1,2,3,4-tetrahydro-1-naphthylidene)propionamide
(E)-2-(7-Fluoro-1,2,3,4-tetrahydro-1-naphthylidene)-N-(2-hydroxyethyl)acetamide
(E)-2-(6-Fluoro-1,2,3,4-tetrahydro-1-naphthylidene)-N-methyl-N-methoxyacetamide
(Z)-N-Cyclopropyl-2-(7-fluoro-1,2,3,4-tetrahydro-2,2-dimethyl-1-naphthylidene)acetamide
(E)-N-Cyclopropyl-2-(7-fluoro-1,2,3,4-tetrahydro-2,2-dimethyl-1-naphthylidene)acetamide
(E)-2-(7-Fluoro-1,2,3,4-tetrahydro-1-naphthylidene)acetanilide
(E)-1-(2-(7-Fluoro-1,2,3,4-tetrahydro-1-naphthylidene)acetyl)azetidine
(E)-1-(2-(7-Fluoro-1,2,3,4-tetrahydro-1-naphthylidene)acetyl)pyrrolidine
(E)-N-Cyclopropyl-2-(1,2,3,4-tetrahydro-7-methyl-1-naphthylidene)acetamide
(E)-N-Cyclopropyl-2-(1,2,3,4-tetrahydro-5-methoxy-1-naphthylidene)acetamide
(Z)-N-cyclopropyl-2-(1,2,3,4-tetrahydro-1-naphthylidene)acetamide
(E)-2-(6-Chloro-1,2,3,4-tetrahydro-1-naphthylidene)-N-cyclopropylacetamide
(Z)-2-(7-Chloro-1,2,3,4-tetrahydro-1-naphthylidene)-N-cyclopropylacetamide
(Z)-N-Cyclopropyl-2-(1,2,3,4-tetrahydro-7-methoxy-1-naphthylidene)acetamide
(Z)-N-Cyclopentyl-2-(7-fluoro-1,2,3,4-tetrahydro-1-naphthylidene)acetamide
(Z)-2-(7-Fluoro-1,2,3,4-tetrahydro-1-naphthylidene)-N-phenylacetamide
(E)-2-(6-Chloro-3,4-dihydro-2H-1-benzopyran-4-ylidene)-N-cyclopropylacetamide
(E)-2-(6-Chloro-3,4-dihydro-2H-1-benzopyran-4-ylidene)-N-methylacetamide
(E)-2-(6-Chloro-3,4-dihydro-2H-1-benzopyran-4-ylidene)acetamide
(E)-N-Cyclopropyl-2-(3,4-dihydro-2H-1-benzothiopyran-4-ylidene)acetamide
(E)-N-2-(3,4-dihydro-2H-1-benzothiopyran4-ylidene)-N-methylacetamide
(E)-2-(3,4-dihydro-2H-1-benzothiopyran-4-ylidene)acetamide
(E)-N-Cyclopropylmethyl-2-(7-fluoro-1,2,3,4-tetrahydro-1-naphthalidene)acetamide and salts, solvates and physiologically functional derivatives thereof.

Other uses of the compounds of the present invention are for the treatment or prophylaxis of conditions associated with:

anxiety,
inflammation,
arthritis and
pain(algesia).

As used herein the term:

a) "physiologically functional derivatives" means any other physiologically acceptable derivative of a compound of the present invention, for example an ester, which, upon administration to the recipient, such as a human, is capable of providing(directly or indirectly) the said compound or an active metabolite or residue thereof.

b) "salt" means acid addition or base salts as further defined hereinbelow.

c) "solvate" means a combination, in definite proportions, of a compound of the present invention with its solvent.

It will be appreciated that the compounds of the present inventions can exist in various geoisomeric forms and as mixtures thereof in any proportions. The present invention includes within its scope such geoisomeric forms or mixtures of geoisomers, including the individual E and Z isomers of the compounds as well as mixtures of such isomers, in any proportions. Preferred compounds of the present invention are those wherein the group adjacent to the exo double bond and the carbonyl group are on opposite sides of the exo double bond. The compounds of the present inventions may exist in forms wherein one or more carbon centers is/are chiral. The present invention includes within its scope each possible optical isomer substantially free, i.e., associated with less than 5%, of any other optical isomer(s), as well as mixtures of one or more optical isomers in any proportion, including racemic mixtures thereof. It will be evident to a skilled person that certain compounds of the present inventions can exist in enantiomeric forms according to the direction of rotation of plane polarized light when passed through a sample of the compound. Individual optical isomers as well as mixtures of such isomers in any proportion are considered to be within the scope of the invention. Pharmaceutically acceptable salts are within the scope of the invention and are particularly suitable for medical applications because of their greater aqueous solubility relative to the parent (i.e., basic) compounds. Such salts must clearly have a pharmaceutically acceptable anion or cation. Suitable pharmaceutically acceptable acid addition salts of the compounds of the present invention include those derived from inorganic acids, such as hydrochloric, hydrobromic, phosphoric, metaphosphoric, nitric, sulphonic and sulphuric acids, and organic acids, such as acetic, benzenesulphonic, benzoic, citric, ethanesulphonic, fumaric, gluconic, glycollic, isothionic, lactic, lactobionic, maleic, malic, methanesulphonic, succinic, p-toluenesulphonic, tartaric and trifluoroacetic acids. The chloride salt is particularly preferred for medical purposes. Suitable pharmaceutically acceptable base salts include ammonium salts, alkali metal salts, such as sodium and potassium salts, and alkaline earth salts, such as magnesium and calcium salts.

Salts having a non-pharmaceutically acceptable anion are also within the scope of the invention as useful intermediates for the preparation or purification of pharmaceutically acceptable salts and/or for use in non-therapeutic, for example, in vitro, applications.

For therapeutic use, acid addition and base salts of compounds according to the present invention will be physiologically acceptable(i.e., they will be salts derived from a physiologically acceptable acid or base). However, salts of acids or bases which are not physiologically acceptable may also find use, for example in the preparation or purification of the compound. All acid and base salts whether or not derived from a physiologically acceptable base are to be considered as being within the scope of the present invention.

A further aspect of the present invention is prodrugs of the compounds of the present invention. Such prodrugs can be metabolised in vivo to give a compound of the present invention. These prodrugs may or may not be active in their own right.

The compounds of the present invention are of particular value in the relaxation of skeletal muscle in spastic, hypertonic and hyperkinetic conditions. In particular the compounds of the present invention can be used in the treatment and symptomatic relief of exertion-induced skeletal muscle spasm, for example, lower back pain. The compounds of the present inventions can also be used for the treatment of conditions such as spinal cord injury, parkinsonism, chorea, arthritis, athetosis, status epilepticus and tetanus and especially in the relief of muscle spasm in conditions such as spasticity, myositis, spondylitis, cerebral palsy, cerebrovascular disease and multiple sclerosis. The compounds can also be used as pre-surgical muscle relaxants.

Convulsive states for which the compounds of the present invention may can be employed include grand mal, petit mal, psychomotor epilepsy and focal seizure. The compounds of the present invention can also be used in the treatment of anxiety including generalised anxiety disorders, obsessive compulsive disorder, panic disorder, phobic anxiety, separation anxiety and post-traumatic stress disorder.

The analgesic activity of compounds of the present invention make them useful to control pain, e.g., pain associated with inflammation and/or trauma. Accordingly, the compounds of the invention have use as mild and strong analgesics.

The compounds of the present invention may can also be used in the treatment of inflammatory arthritic conditions, including rheumatoid arthritis, rheumatoid spondylitis, osteoarthritis, gouty arthritis, as well as non-articular inflammatory conditions, including herniated/ruptured/prolapsed intervertebral disk syndrome, bursitis, tendinitis, tenosynovitis, fibromyalgia syndrome and other inflammatory conditions associated with ligamentous sprain and regional musculoskeletal strain. It is particularly noted that compounds of the present invention exhibit reduced occurence of ulcerogenicity, as compared with other anti-inflammatory agents, such as ibuprofen, naproxen or asprin.

The compounds of the invention are also useful as anti-anxiety agents.

In a further aspect of the present invention there is included:

(a) compounds of the present invention or pharmaceutically acceptable salts, solvates or physiologically functional derivatives thereof for use as therapeutic agents, particularly in the prophylaxis or treatment of clinical conditions conditions associated with abnormally raised muscle tone, convulsive states, anxiety, inflammation, arthritis or pain.

(b) pharmaceutical compositions comprising a compounds of the present invention or pharmaceutically acceptable salts, solvates, or physiologically functional derivatives thereof, at least one pharmaceutically acceptable carrier therewith, and optionally one or more other physiologically active agents.

(c) a method for the treatment or prophylaxis of conditions associated with abnormally raised muscle tone, convulsive states, anxiety, inflammation, arthritis or pain in a host, for example, a mammal including a human, comprising administering to the host an effective treatment amount of a compounds of the present invention.

(d) use of a compound of the present invention in the manufacture of a medicament for the treatment or prophylaxis of conditions associated with abnormally raised muscle tone, convulsive states, anxiety, inflammation, arthritis or pain.

(e) processes for the preparation of compounds of the present invention and intermediates thereof (including salts, solvates or physiologically functional derivatives thereof as defined herein).

The above compounds can be employed in combination with other therapeutic agents for the treatment of the conditions associated with abnormally raised muscle tone. Examples of such other therapeutic agents include analgesics, such as, codeine, acetaminophen, phenacetin or ibuprofen. The compounds according to the invention can also be employed in combination with other therapeutic agents for the treatment of conditions associated with inflammation, arthritis, and/or pain. Examples of such other therapeutic agents include analgesics, such as codeine, oxycodone, acetaminophen, phenacetin, or ibuprofen; antiarthritics, such as methotrexate or azathioprine; and decongestants, such as ephedrine or pseudoephedrine.

The present invention further provides pharmaceutical compositions of the compounds of the present invention also referred to herein as active ingredients, which may be administered for therapy by any suitable mute including oral, rectal, nasal, topical (including buccal and sublingual), vaginal and parenteral (including subcutaneous, intramuscular, intravenous and intradermal). It will also be appreciated that the preferred route will vary with the conditions and age of the recipient, the nature of the disorder and the chosen active ingredient.

The mount required of the individual active ingredient for the treatment of, for example, increased muscle tone, inflammation, arthritis, and/or pain of course depends upon a number of factors including the severity of the condition to be treated and the identity of the recipient and will ultimately be at the discretion of the attendant physician.

In general, for the foregoing conditions a suitable dose of a compound of the present invention or salts, solvates or physiologically functional derivatives thereof (estimated as the parent compound) is in the range of 0.05 to 100 mg per kilogram body weight of the recipient per day, preferably in the range of 0.1 to 50 mg per kilogram body weight per day, most preferably in the range 0.5 to 20 mg per kilogram body weight per day and optimally 1 to 10 mg per kilogram body weight per day. The desired dose is preferably presented as two, three, four, five, six or more sub-doses administered at appropriate intervals throughout the day. These sub-doses may be administered in unit dosage forms, for example, containing 1 to 1500 mg, preferably 5 to 1000 mg, and most preferably 10 to 700 mg of active ingredient per unit dosage form.

While it is possible for the active ingredient to be administered alone it is preferable to present it as a pharmaceutical composition. The compositions of the present invention comprises at least one active ingredient, as defined above, together with one or more acceptable carriers thereof and optionally other therapeutic agents. Each carrier must be "acceptable" in the sense of being compatible with the other ingredients of the composition and not injurious to the recipient.

Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, cachets or tablets each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example hydroxypropylmethyl cellulose in varying proportions to provide the desired release profile. Tablets may optionally be provided with an enteric coating, to provide release in parts of the gut other than the stomach.

Compositions suitable for oral use as described above may also include buffering agents designed to neutralize stomach acidity. Such buffers may be chosen from a variety of organic or inorganic agents such as weak acids or bases admixed with their conjugated salts.

Compositions suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Compositions for rectal administration may be presented as a suppository with a suitable base comprising for example cocoa butter or a salicylate.

Compositions suitable for vaginal administration may be presented as pessaries, tampons, creams, gels pastes, foams or spray formulations containing in addition to the active ingredient such carriers as are known in the art to be appropriate.

Compositions suitable for parenteral administration include aqueous and non-aqueous isotonic sterile injections solutions which may contain anti-oxidants, buffers, bacteriostats and solutes which render the compositions isotonic with the blood of the intended recipient; and aqueous and non-aqueous sterile suspensions which may include suspending agents and thickening agents, as liposomes or other microparticulate systems which are designed to target the compounds to blood components or one or more organs. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compositions suitable for transdermal administration may be presented as discrete patches adapted to remain in intimate contact with the epidermis of the recipient for a prolonged period of time. Such patches suitably contain the active compound as an optionally buffered, aqueous solution of, for example, 0.1 to 0.2M concentration with respect to the said compound. As one particular possibility, the active compound may be delivered from the patch by iontophoresis as generally described in *Pharmaceutical Research*, 3(6), 318 (1986).

Preferred unit dosage compositions are those containing a daily dose or unit, daily sub-dose, as herein above recited, or an appropriate fraction thereof, of an active ingredient.

It should be understood that in addition to the ingredients particularly mentioned above the compositions of this invention may include other agents conventional in the art having regard to the type of composition in question, for example, those suitable for oral administration may include such further agents as sweeteners, thickeners and flavoring agents.

The compounds of the invention can be prepared in any conventional manner and in accordance with the present invention, can, for example, be prepared by the methods hereinafter described.

EXAMPLE 1

Preparation of (E)-2-(6-Fluoro-1-indanylidene) acetamide a) Preparation of 3-(4-Fluorophenyl)propionic Acid A mixture of 4-fluorocinnamic acid (300.0 g, 1.8 mol, Aldrich) and 5% palladium on carbon (9.0 g) in ethanol (3 L) was hydrogenated at atmospheric pressure and room temperature for 4.5 h. The mixture was filtered through Celite (diatomaceous earth) and the filtrate was concentrated in vacuo to give 275.1 g (91%) of 3-(4-fluorophenyl) propionic acid as a white solid, m.p., 86°–88° C.; NMR (DMSO-$d_6$): d12.15 (br s, 1H, COOH), 7.07–7.29 (m,4H, Ar), 2.81(t, 2H, $CH_2CO$), 2.52 (t,2H, $ArCH_2$).

Anal. Calcd. for $C_9H_9FO_2$: C,64.28; H,5.39. Found: C,64.23; H, 5.42.

b) Preparation of 3-(4-Fluorophenyl)propionyl Chloride

A mixture of 3-(4-fluorophenyl)propionic acid (275.1 g, 1.6 mol) and thionyl chloride (300 mL, 4.1 mol) was heated to reflux for 3 h, cooled to room temperature and distilled under aspirator vacuum to give 287.6 g (96%) of 3-(4-fluorophenyl)propionyl chloride as a pale pink oil, b.p., 120°–122° C./15 mm Hg; IR (neat) 1793,1511 $cm^{-1}$; NMR (DMSO-$d_6$): d7.04–7.32 (m, 4H, Ar), 2.50–2.89 (m, 4H, $2XCH_2$).

Anal. Calcd. for $C_9H_8ClFO$: C,57.93; H,4.32; Cl, 19.00. Found: C,57.86; H,4.34; Cl,18.90.

c) Preparation of 6-Fluoro-1-indanone

A solution of 3-(4-fluorophenyl)propionyl chloride (287.6 g, 1.5 mol) in dichloromethane (1.4 L) was added dropwise during 3 h to an ice-cold, mechanically stirred suspension of aluminum chloride (226.0 g, 1.7 mol, Aldrich) in dichloromethane (2.2 L) under nitrogen. The resulting yellowish-black solution was refluxed for 5 h and allowed to cool to room temperature. The solution was washed successively with water (2 L), 1N sodium hydroxide (2 L), water (2 L) and brine (2 L). The organic layer was dried over anhydrous sodium sulfate, filtered and concentrated to a tan solid (229.1 g, 99%). The solid was recrystallized from dichloromethane-hexane to give 215.7 g (93%) of 6-fluoro-1-indanone as off-white crystals, m.p., 57°–59° C.; NMR (DMSO-$d_6$): d 7.36–7.66 (m, 3H, Ar), 2.65–2.72, 3.06–3.10 (2m's, 4H, $2XCH_2$).

Anal. Calcd. for $C_9H_7FO$: C,71.99; H,4.70. Found: C, 71.94; H, 4.72.

d) Preparation of Ethyl 2-(6-Fluoro-1-hydroxy-1-indanyl) acetate

A mixture of 6-fluoro-1-indanone (5.0 g, 33.3 mmol), ethyl bromoacetate (8.3 g, 50.0 mmol, Aldrich), activated zinc powder (3.2 g, 50.0 mmol, Mallinckrodt; Org. Synth., Coll. Vol. 6, 290, 1988) and a few crystals of iodine in diethyl ether-benzene (1:1, 100 mL) was heated at reflux under nitrogen for 24 h. The mixture was filtered and the filtrate was concentrated in vacuo. The residue in diethyl ether was vigorously stirred with excess dilute ammonium hydroxide, dried and concentrated to give ethyl 2-(6-fluoro-1-hydroxy-1-indanyl)acetate as an amber oil (7.6 g, 97%); NMR (DMSO-$d_6$): d 6.99–7.24 (m, 3H, Ar), 5.38 (s, 1H, OH), 4.00 (q, 2H, $CH_2CH_3$), 2.64–2.92 (m, 4H, $2XCH_2$), 2.45–2.54, 2.05–2.14 (2m's, 2H, $CH_2CO$), 1.08 (t,3H, $CH_3$).

Anal. Calcd. for $C_{13}H_{15}FO_3$: C, 65.54; H, 6.35. Found: C, 65.36; H, 6.39.

e) Preparation of Ethyl 2-(6-Fluoro-1-hydroxy-1-indanyl) acetate

Ethyl acetate (1.8 g, 20 mmol) was added dropwise to a stirred, chilled (dry ice-acetone bath) 1N solution of lithium bis(trimethylsilyl)amide in tetrahydrofuran (20 mL, Aldrich) under nitrogen. After 15 min, a solution of 6-fluoro-1-indanone (3.0 g, 20 mmol) in tetrahyrofuran (20 mL) was added dropwise and the resulting mixture was stirred for 1h (dry ice-acetone bath). A 1N solution of hydrochloric acid (20 mL) was added and the mixture was allowed to warm to more temperature. The organic phase was separated, dried over anhydrous sodium sulfate, filtered and concentrated to a pale yellow oil (5.3 g). The mixture was chromatographed on Silica Gel 60 (silica gel) using a linear gradient of dichloromethane- hexanes (1:1) to dichloromethane as eluent. The fractions containing only ethyl 2-(6-fluoro-1-hydroxy-1-indanyl)acetate were combined and concentrated in vacuo to give 3.1 g (65%) of a colorless oil; NMR (DMSO-$d_6$): d 6.98–7.27 (m, 3H, Ar), 5.40 (s, 1H, OH), 4.01 (q, 2H, $OCH_2$), 2.64–2.96 (m, 4H, $2XCH_2$), 2.44–2.57 (m, 1H, CH), 2.04–2.18 (m, 1H, CH), 1.12 (t, 3H, $CH_3$).

Anal. Calcd for $C_{13}H_{15}FO_3$: C, 65.54; H, 6.35. Found: C, 65.44; H, 6.38 f) Preparation of 2-(6-Fluoro-1-hydroxy-1-indanyl)acetic Acid

A mixture of ethyl 2-(6-fluoro-1-hydroxy-1-indanyl) acetate (44.0 g, 0.18 mol), 1N sodium hydroxide (180 mL) and absolute ethanol (280 mL) was stirred for 18 h at room temperature. The mixture was concentrated in vacuo, diluted with $H_2O$ and extracted with diethyl ether. The aqueous phase was acidified (pH 3) with dilute hydrochloric acid and extracted with diethyl ether. The diethyl ether layer was washed with brine, dried over sodium sulfate, filtered and concentrated in vacuo to give 2-(6-fluoro-1-hydroxy-1-indanyl)acetic acid as an amber oil (37.7 g, 100%; Note: This compound spontaneously dehydrated upon standing at room temperature to a mixture of olefins unless immediately reacted with trifluoroacetic acid); NMR (DMSO-$d_6$): d 11.60 (br s, 1H, COOH), 6.75–7.05 (m, 3H, Ar), 5.20 (br s, 1H, OH), 2.22–2.69, 1.77–1.95 (2m's, 6H, $3XCH_2$).

Anal. Calcd. for $C_{11}H_{11}FO_3$: C, 62.85; H, 5.27. Found: C, 62.57; H, 5.30.

g) Preparation of Lithium 2-(6-Fluoro-1-hydroxy-1-indanyl)acetate

A mixture of ethyl 2-(6-fluoro-1-hydroxy-1-indanyl) acetate (2.0 g. 8.4 mmol), 1N lithium hydroxide (8.4 mL) and absolute ethanol (13.0 mL) was stirred for 18h at room temperature. The mixture was concentrated in vacuo, diluted with $H_2O$ and extracted with diethyl ether. The aqueous phase was concentrated in vacuo, diluted with toluene (100 mL) and concentrated in vacuo to give lithium 2-(6-fluoro-1-hydroxy-1-indanyl)acetate as a white solid (1.4 g, 77%); NMR (DMSO-$d_6$): d 8.90 (s, 1H, OH), 6.88–7.18 (m, 3H, Ar), 2.55–2.83 (m, 2H, $ArCH_2$), 2.13 (s, 2H, $CH_2CO$), 1.88–2.07 (m, 2H, $CH_2$).

Anal. Calcd. for $C_{11}H_{10}FLiO_3$—0.15 $H_2O$: C,60.37; H, 4.74 Found: C, 60.32; H, 4.70 h) Preparation of (E)-2-(6-Fluoro-1-indanylidene)acetic Acid

Trifluoroacetic acid (1.5 mL) was added to a stirred, chilled (ice-methanol bath) suspension of lithium 2-(6-fluoro-1-hydroxy-1-indanyl)acetate (0.5 g, 2.3 mmol) in dichloromethane (13.5 mL). After 15 min, the mixture was concentrated in vacuo and the resulting white solid was recrystallized from aqueous acetone to give (E)-2-(6-fluoro-1-indanylidene)acetic acid as white crystals (0.32 g, 73%) identical to compound of Example 1i by mixed m.p., (203°–205° C.) and NMR.

Anal. Calcd. for $C_{11}H_9FO_2$: C,68.75; H,4.72 Found: C,68.67; H,4.75 i) Preparation of (E)-2-(6-Fluoro-1-indanylidene)acetic Acid

Trifluoroacetic acid (100 mL) was added to a stirred, chilled (ice-methanol bath) solution of 2-(6-Fluoro-1-hydroxy-1-indanyl)acetic acid (37.5 g, 0.18 mol) in dichloromethane (900 mL). After 15 min, the mixture was concentrated in vacuo to give (E)-2-(6-fluoro-1-indanylidene) acetic acid as a yellowish-tan solid (33.0 g, 95%), m.p., 203°–205° C.; NMR (DMSO-$d_6$): d 12.05 (br s, 1H, COOH), 7.16–7.65 (m, 3H, Ar), 6.37 (t,1H, =CH), 2.94–2.98, 3.15–3.20 (2m's, 4H, 2XCH$_2$); steady-state nOe: :irradiation at 6.37 d, observed 24% nOe at 7.65 d.

Anal. Calcd. for C11H$_9$FO$_2$: C,68.75; H,4.72. Found: C,68.65; H,4.68.

j) Preparation of (E)-2-(6-Fluoro-1-indanylidene)acetyl Chloride

An ice-cold, stirred suspension of (E)-2-(6-fluoro-1-indanylidene) acetic acid (384 mg, 2 mmol) in benzene (10 mL) was treated with oxalyl chloride (761 mg, 6 mmol) and allowed to warm to room temperature during 1.5 h. The resulting yellow solution was concentrated in vacuo to give (E)-2-(6-fluoro-1-indanylidene)acetyl chloride as a pale yellow solid (421 mg, 100%), m.p., 97°–99° C.; IR (Nujol (high boiling petroleum oil)): 1750, 1600 cm$^{-1}$; NMR (DMSO-$d_6$): d 7.18–7.67 (m, 3H, Ar), 6.39 (t, 1H, =CH), 2.96–2.99, 3.16–3.21 (2m's, 4H, 2XCH$_2$).

Anal. Calcd. for $C_{11}H_8ClFO$: C, 62.73; H, 3.83; Cl, 16.83. Found: C, 62.83; H, 3.87; Cl, 16.76.

k) Preparation of (E)-2-(6-Fluoro- 1-indanylidene) acetamide

A 29.6% aqueous ammonium hydroxide solution (17.6 mL, 134 mmol) was added dropwise to a stirred, chilled (ice bath) solution of (E)-2-(6-fluoro-1-indanylidene)acetyl chloride (14.1 g, 67 mmol) in dichloromethane (165 mL). After an hour, the resulting white precipitate was collected by filtration, dissolved in ethyl acetate (600 mL) and washed with water (3×300 mL). The ethyl acetate layer was dried over sodium sulfate and concentrated in vacuo. The resulting off-white solid was washed with hexane, giving 11.6 g (91%) of (E)-2-(6-fluoro-1-indanylidene)acetamide, m.p., 180°–183° C.; NMR (DMSO-$d_6$): d6.91–7.41 (m, 5H, Ar+NH$_2$), 6.37 (t,1H, =CH), 2.92–2.96, 3.16–3.22 (2m's, 4H, 2XCH$_2$); steady-state nOe:irradiation at 6.37 d, observed 23% nOe at 7.28 d.

Anal. Calcd. for $C_{11}H_{10}FNO$: C,69.10; H,5.27; N, 7.33. Found: C, 69.02; H, 5.33; N, 7.29.

EXAMPLE 2

Preparation of (E)-N-Cyclopropyl-2-(6-fluoro-1-indanylidene)acetamide

To an ice-cold stirred solution of (E)-2-(6-Fluoro-1-indanylidene)acetyl Chloride in dichloromethane (50 ml) was added cyclopropylamine (1.65 g, 28.86 mmol) and the reaction was warmed to room temperature overnight. The reaction was evaporated in vacuo to a solid residue. This residue was dissolved in ethyl acetate (300 ml), washed with water (75 ml), and the organic layer was concentrated by spin evaporation in vacuo. The residue was chromatographed on silica gel using ethyl acetate-hexanes (0:1 to 1:1 gradient) as eluent. Fractions containing only the product were combined and concentrated by spin evaporation in vacuo. Recrystallization of the residue from dichloromethane-hexanes gave 1.6 g (76%) of (E)-N-cyclopropyl-2-(6-fluoro-1-indanylidene)acetamide as a white powdery solid, m.p. 124°–127° C.; NMR (DMSO-$d_6$): d 8.03 (d, 1H, J=3.9 Hz, NH), 7.45–7.38 (m, 1H, Ar), 7.28–7.14 (m,2H, Ar), 6.30 (s, 1H, =CH, 3.23–3.21 (m, 2H, CH$_2$), 2.99–2.96 (m, 2H, CH$_2$), 2.72 (m, 1H, NCH), 0.71–0.39 (2ms, 4H, CH$_2$–CH$_2$); steady state nOe: irradiation at d6.30, observed 15% nOe at d 8.03 and 20% nOe at d 7.23.

Anal. Calcd for $C_{14}N_{14}FNO$: C, 72.71; H, 6.10; N, 6.06. Found: C, 72.54; H, 6.13; N, 6.01.

EXAMPLE 3 (REFERENCE EXAMPLE)

Preparation of (E)-2-(7-Fluoro-1,2,3,4-tetrahydro-1-naphthylidene)acetic Acid a) Preparation of Ethyl 2-(7-Fluoro-1,2,3,4-tetrahydro-1-hydroxy-1-naphthyl)acetate Ethyl acetate (5.4 g, 61 mmol) was added dropwise to a stirred, chilled (dry ice-acetone bath) solution of 1M lithium bis(trimethylsilyl)amide in tetrahydrofuran (61 mL, 0.061 mol, Aldrich) under nitrogen. After 15 min, a solution of 7-fluoro-1-tetralone (10.0 g, 61 mmol) in tetrahydrofuran (25 mL) was added dropwise and the resulting mixture was stirred for 1h (dry ice-acetone bath). A 1N solution of hydrochloric acid (61 mL) was added and the mixture was allowed to warm to room temperature. The organic phase was separated, dried over anhydrous sodium sulfate, filtered and concentrated to a pale yellow oil (15.0 g, 100%). An analytical sample was obtained by chromatographing a 1.5 g portion on Silica Gel 60 using dichloromethane-hexanes (1:1) as eluent. The fractions containing only ethyl 2-(7-fluoro-1,2,3,4-tetrahydro-1-hydroxy-1-naphthyl)acetate were combined and concentrated in vacuo to give 1.2 g (80%) of a colorless oil; NMR (DMSO-$d_6$): d 6.93–7.31 (m, 3H, Ar), 5.28 (s, 1H, OH), 3.98 (m, 2H, CH$_2$OOC), 2.60–2.87 (m, 4H, CH$_2$CO, CH$_2$), 2.12–2.28 (m, 1H, CH), 1.78–1.86 (m, 3H, CH, CH$_2$), 1.09 (t, 3H, CH$_3$).

Anal. Calcd. for $C_{14}H_{17}FO_3$: C, 66.65; H, 6.79. Found: C, 66.64; H, 6.82.

b) Preparation of Ethyl 2-(7-Fluoro-1,2,3,4-tetrahydro-1-naphthyl)acetate

Trifluoroacetic acid (20 mL) was added to a stirred, chilled (ice-methanol bath) solution of crude ethyl 2-(7-fluoro-1,2,3,4-tetrahydro-1-hydroxy-1-naphthyl)acetate (10.0 g, 35.8 mmol) in dichloromethane (180 mL). After 4h, the mixture was concentrated in vacuo to a clear oil (8.3 g, 100%); NMR (DMSO-$d_6$): d 6.94–7.65 (m, 3H, Ar), 6.45 (br s, 0.2 H, =CH/E), 6.10 (t, 0.8H, =CH/endo), 4.08 (m, 2H, CH$_2$OOC), 3.67, 3.51 (s's, 2.2H, H$_2$O, CH$_2$/endo), 3.08, 2.70, 2.25, 1.77 (m's, 4.4H, 5xCH$_2$), 1.26 (t, 0.6H, CH$_3$/E), 1.17 (t, 2.4H, CH$_3$/endo).

Anal. Calcd. for $C_{14}H_{15}FO_2$·0.3 H$_2$O: C,70.16; H,6.56. Found: C, 70.03; H, 6.34.

A portion of the above mixture of E and endo esters (2.3 g, 10 mmol), sodium hypophosphite hydrate (1.8 g, 20 mmol, Aldrich) and 10% palladium on carbon (0.2 g) in 75% aq ethanol (20 mL) was heated to reflux for 2h. The mixture was filtered through celite and the filtrate was concentrated in vacuo. The residue in dichloromethane was washed successively with water (100 mL) and brine (50 mL), dried over anhydrous sodium sulfate, filtered, concentrated in vacuo and chromatographed on Silica Gel 60 using ethyl acetate-hexane (3:97) as eluent. The fractions containing only ethyl 2-(7-fluoro-1,2,3,4-tetrahydro-1-naphthyl)acetate were combined and concentrated in vacuo to give 1.9 g (78%) of a pale yellow oil; NMR (DMSO-$d_6$): d 6.89–7.14 (m, 3H, Ar), 4.11 (q, 2H, $CH_2OOC$), 3.15–3.17 (m, 1H, CH), 2.44–2.82 (m, 4H, 2×$CH_2$), 1.52–1.90 (m, 4H, 2×$CH_2$), 1.20 (t, 3H, $CH_3$).

Anal. Calcd. for $C_{14}H_{17}FO_2$: C, 71.17; H, 7.25. Found: C, 71.25; H, 7.26.

c) Preparation of Ethyl 2-Bromo-2-(7-fluoro-1,2,3,4-tetrahydro-1-naphthy)acetate To a stirred, chilled (dry ice-acetone bath) solution of diisopropylamine (0.3 mL, 1.9 mmol, Aldrich) in tetrahydrofuran (3 mL) under nitrogen was successively added 2.5N n-butyl lithium in hexane (0.8 mL, Aldrich), chlorotrimethylsilane (0.2 mL, 1.8 mmol, Aldrich) and ethyl 2-(7-fluoro-1,2,3,4-tetrahydro-1-naphthyl)acetate (236 mg, 1.0 mmol). The resulting clear solution was stirred for 1h, treated with N-bromosuccinimide (180 mg, 1.0 mmol, Aldrich) and stirred for an additional 0.5h before the dry ice-acetone bath was removed. The reddish cloudy solution was stirred for 2h at room temperature, treated with dilute aq hydrochloric acid (4 meq) and extracted with diethyl ether (30 mL). The ether layer was dried over anhydrous sodium sulfate, filtered, concentrated in vacuo and chromatographed on Silica Gel 60 using dichloromethane-hexane (1:9) as eluent. Fractions containing only ethyl 2-bromo-2-(7-fluoro-1,2,3,4-tetrahydro-1-naphthyl)acetate as a 1:4 isomeric mixture were combined and concentrated in vacuo to a clear oil (171 mg, 54%); NMR (DMSO-$d_6$): d 7.00–7.18 (m, 3H, Ar), 5.20 (d, J=6.2 Hz, 0.8H, BrCHCO), 5.17 (d, J=6.2 Hz, 0.2H, BrCHCO), 4.19 (q, 1.6H, $CH_2OOC$), 4.14 (q, 0.4H, $CH_2OOC$), 3.49 (m, 1H, ArCH), 2.69 (m, 2H, Ar$CH_2$), 1.81–1.97 (m, 3H, CH, $CH_2$), 1.61–1.67 (m, 1H, CH), 1.21 (t, 2.4H, $CH_3$), 1.07 (t, 0.6H, $CH_3$).

Anal. Calcd. for $C_{14}H_{16}BrFO_2$: C, 53.35; H, 5.12; Br, 25.35. Found: C, 53.44; H, 5.09; Br, 25.32.

d) Preparation of (E)-2-(7-Fluoro-1,2,3,4-tetrahydro-1-naphthylidene)acetic Acid A mixture of ethyl 2-bromo-2-(7-fluoro-1,2,3,4-tetrahydro-1-naphthyl)acetate (2.2 g, 7.0 mmol), 1N potassium tert-butoxide in tetrahydrofuran (14 mL, Aldrich) and tert-butanol (140 mL) was stirred for 5h at room temperature. The resulting suspension was concentrated in vacuo, diluted with water (200 mL) and washed with diethyl ether. The aqueous layer was acidified by adding 1N hydrochloric acid (14 mL) and extracted with diethyl ether. The ether extract was dried over anhydrous sodium sulfate, filtered, concentrated in vacuo and chromatographed on Silica Gel 60 using ethyl acetate-hexane (1:1) as eluent. The fractions containing only (E)-2-(7-fluoro-1,2,3,4-tetrahydro-1-naphthylidene)acetic acid were combined and concentrated in vacuo to give a white solid (0.8 g, 55%); NMR (DMSO-$d_6$): d 12.22 (br s, 1H, COOH), 7.57 (d of d, $J_m$=2.6 Hz, $J_o$=11.0 Hz, 1H, Ar), 7.12–7.28 (m, 2H, Ar), 6.36 (s, 1H, =CH, E), 3.04 (t, 2H, Ar$CH_2$), 2.74 (t, 2H, $CH_2$), 1.74 (m, 2H, $CH_2$); steady-state nOe: irradiation at 6.36, observed 25% nOe at 7.57.

Anal Calcd. for $C_{12}H_{11}FO_2$: C, 69.89; H, 5.38. Found: C, 69.88; H, 5.38.

EXAMPLE 4 (REFERENCE EXAMPLE)

Preparation of (E)-2-(6-Fluoro-3,3-dimethyl-1-indanylidene)acetamide a) Preparation of Diethyl Isopropylidenemalonate Diethyl isopropylidenemalonate was prepared according to the procedure of E. L. Eliel, R. O. Hutchins, and Sr. M. Knoeber, Organic Synthesis Coll. Vol. VI, 442, 1988, with following modifications. A mixture of acetone (54 g, 0.93 mol, Mallinckrodt), diethyl malonate (100 g, 0.62 mol, Aldrich), acetic anhydride (80 g, 0.78 mol, Mallinckrodt), and zinc chloride (12.5 g, 0.78 mol, Aldrich) was refluxed (90° C. oil bath) for 18 h while protected from moisture. The reaction solution was diluted with dichloromethane (500 ml) and washed with cold water (3×50 ml). The aqueous washes were combined and extracted with dichloromethane. All dichloromethane layers were combined and concentrated by spin evaporation in vacuo. The residual oil was distilled under vacuum and the fractions boiling at 102°–138° C. at 12 Torr were combined with the pot residue and heated for 6 h with a 200° C. oil bath. The dark oil was redistilled to give 40.1 g (32%) of diethyl isopropylidenemalonate as a clear oil: b.p., 110°–115° C./12 mm Hg: NMR (DMSO-$d_6$): d 4.19 (q, 4 H, J=7.2 Hz, $OCH_2$), 2.03 (s, 6 H, =C($CH_3$)$_2$), 2.25 (t, 6 H, J=7.2 Hz, $CH_2$).

EXAMPLE 5

Preparation of (Z)-2-(2-bromo-6-fluoro-1-indanylidene)acetamide

N-Bromosuccinimide (22.57 g, 126.8 mmoles, Aldrich) and benzoyl peroxide (1.89 g, 7.8 mmoles, Aldrich) were added to a suspension of (E)-2-(6-fluoro-1-indanylidene)acetamide (21.00 g, 109.8 mmoles) in carbon tetrachloride (400 mL) and benzene (400 mL). The mixture was refluxed under a calcium chloride drying tube while shining an infrared lamp on it for two hours, after which time an orange solution formed. The heat and light were removed, and the solution was stirred at ambient temperature for 18 hours. The mixture was filtered, and the solids were washed with ethyl acetate. The washings and filtrate were combined and evaporated in vacuo. The residue was dissolved in ethyl acetate (800 mL) and washed with water (3×200 mL) and brine (200 mL), dried over sodium sulfate, filtered and evaporated in vacuo. The residue was chromatographed on silica gel eluting first with hexane: ethyl acetate (2:1) gradually increasing the polarity to hexane: ethyl acetate (1:1). The fractions containing the major spot were combined and evaporated in vacuo to give a yellow solid which was dried in a vacuum at 70° C. for 18 hours to give 1.022 g (3%) of (Z)-2-(2-bromo-6-fluoro-1-indanylidene)acetamide as a yellow solid, mp 162°–163° C. $^1$H-NMR (DMSO-$d_6$): d7.19–7.85 (m, 5H), 6.46 (s, 1H), 6.32 (d, 1H, J=5.7 Hz), 3.64 (dd, 1H, J=5.6 Hz, 18.4 Hz) and 3.27 (d, 1H, J=18.5 Hz); steady-state nOe: irradiation at 6.46 d, observed 21% nOe at 7.39 d.

Anal. Calcd. for $C_{11}H_9BrFNO$ (mw 270.095 ): C, 48.91; H, 3.36; N, 5.19; Br, 29.58. Found: C, 49.02; H, 3.35; N, 5.16; Br, 29.50.

EXAMPLE 6

Preparation of (Z)-2-(2,3-dibromo-6-fluoro-1-indanylidene)acetamide

N-Bromosuccinimide (49.37 g, 277.4 mmoles, Aldrich) and benzoyl peroxide (1.60 g, 6.6 mmoles, Aldrich) were added to a suspension of (E)-2-(6-fluoro-1-indanylidene) acetamide (17.68 g, 92.5 mmoles) in carbon tetrachloride (335 mL) and benzene (335 mL). The mixture was refluxed under a calcium chloride drying tube for four hours, after which time an orange solution formed. The heat was removed, and the solution was stirred at ambient temperature for 18 hours. The mixture was filtered, and the solids were washed with ethyl acetate. The washings and filtrate were combined and evaporated in vacuo. The residue was dissolved in ethyl acetate (800 mL) and washed with water (3×200 mL) and brine (200 mL), dried over sodium sulfate, filtered and evaporated in vacuo. The residue was chromatographed on silica gel eluting with hexane:ethyl acetate (2:1). The fractions containing the compound with Rf=0.4 in hexane:ethyl acetate (1:1) were combined and chromatographed again on silica gel eluting with hexane:ethyl acetate (2:1). The fractions containing the compound with Rf=0.4 in hexane:ethyl acetate (1:1) were combined and evaporated in vacuo to give a solid which was washed with hexane and dried in a vacuum at 50° C. for 18 hours to give 1.35 g (4%) of (Z)-2-(2,3-dibromo-6-fluoro-1-indanylidene)acetamide as a yellow solid, mp 158°–163° C. (decomposed). $^1$H-NMR (DMSO-d$_6$): d 7.35–7.70 (m, 5H), 6.68 (s, 1H), 6.53 (s, 1H), 5.99 (s, 1H).

Anal. Calcd. for $C_{11}H_8Br_2FNO$ (row 348.985): C, 37.85; H, 2.31; N, 4.01. Found: C, 37.98; H, 2.26; N, 4.03.

EXAMPLE 7 (REFERENCE EXAMPLE)

Preparation of (Z)-2-(6-fluoro-2-hydroxy-1-indanylidene)acetamide (Method A)

A mixture of (Z)-2-(2-bromo-6-fluoro-1-indanylidene) acetamide (5.30 g, 19.25 mmoles) and silver nitrate (10.40 g, 61.18 mmoles, Aldrich) in dimethoxyethane (265 mL) and water (100 mL) was refluxed for 18 hours. The mixture was filtered, and the filtrate was diluted with water (700 mL) and extracted with ethyl acetate (6×100 mL). The combined extracts were washed with water (200 mL) and brine (200 mL), dried over magnesium sulfate, filtered, and evaporated in vacuo. The residue was chromatographed on silica gel, eluting with hexane:ethyl acetate (2:1), gradually increasing the polarity to hexane:ethyl acetate (1:1). The fractions containing the compound with Rf=0.18 were combined and evaporated in vacuo to give 1.13 g (28%) of crude (Z)-2-(6-fluoro-2-hydroxy-1-indanylidene)acetamide as an orange solid. Recrystallization from ethyl acetate:hexane mixtures gave 0.49 g (12%) of (Z)-2-(6-fluoro-2-hydroxy-1-indanylidene)acetamide as an off-white solid, mp 201°–202° C.; $^1$H-NMR (DMSO-d$_6$): d 7.73 (d, 2H), 7.19–7.39 (m, 3H), 6.53 (m, 1H), 6.47 (m, 1H), 5.23 (m, 1H), 3.33 (dd, 1H, J=9.6 Hz, 17.0 Hz), and 2.81 (dd, 1H, J=1.6 Hz, 16.3 Hz); steady-state nOe: irradiation at 6.47 d, observed 20% nOe at 7.38 d.

Anal. Calcd. for $C_{11}H_{10}FNO_2$ (mw 207.20): C, 63.76; H, 4.86; N, 6.76. Found: C, 63.77; H, 4.89; N, 6.73.

Preparation of (Z)-2-(6-fluoro-2-hydroxyl-1-indanylidene)acetamide (Method B)

A suspension of (E)-2-(6-fluoro-1-indanylidene) acetamide (12.00 g, 62.8 moles) in dichloromethane (250 mL) was added to a solution of selenium dioxide (5.20 g, 46.9 mmoles, Aldrich) and tert-butyl hydroperoxide (25 mL, 260.8 mmoles, Aldrich) in dichloromethane (500 mL). The suspension was stirred at ambient temperature for 3 days. Additional tert-butyl hydroperoxide (10 mL, 104.3 moles) was added, and the mixture was stirred at ambient temperature for 18 hours. Additional selenium dioxide (5.00 g, 45.1 mmoles) was added, and the mixture was stirred at ambient temperature for 18 hours. Additional tert-butyl hydroperoxide (15 mL, 156.5 mmoles) was added, and the mixture was stirred at ambient temperature for 18 hours. The mixture was filtered to remove about one gram of impure product, and the filtrate was dried over magnesium sulfate, filtered, and evaporated in vacuo. Additional selenium dioxide (5.00 g, 45.1 mmoles) was added, and the mixture was stirred at ambient temperature for 18 hours. The mixture was concentrated in vacuo to 300 mL, hexane was added, and the precipitate was collected by filtration, washed with hexane, and combined with the solids collected previously. The combined solids were dissolved in ethyl acetate (700 mL), washed successively with water (3×100 mL) and brine (100 mL), concentrated in vacuo to 100 mL, and cooled in an ice bath. The solids were collected by filtration, and the filtrate was concentrated in vacuo to give a second crop of solids. All of the solids were combined and chromatographed on silica gel, eluting with hexane:ethyl acetate (1:1). The fractions containing the major spot were combined and evaporated in vacuo to give 5.80 g of an off-white solid, which was washed with chloroform (3×50 mL) to give 5.43 g (42%) of (Z)-2-(6-fluoro-2-hydroxy-1-indanylidene)acetamide as a white solid; mp 202°–204° C.; $^1$H-NMR (DMSO-d$_6$): d 7.76 (d, 1H), 7.19–7.43 (m, 3H), 6.53 (m, 1H), 6.48 (m, 1H), 5.25 (m, 1H), 3.33 (dd, 1H, J=7.8 Hz, 17.0 Hz), and 2.81 (dd, 1H, J=3.2 Hz, 16.8 Hz).

Anal. Calcd. for $C_{11}H_{10}FNO_2$ (mw 207.20): C, 63.76; H, 4.86; N, 6.76. Found: C, 63.82; H, 4.83; N, 6.79.

EXAMPLE 8

Preparation of (Z)-2-(6-fluoro-2-nitrooxy-1-indanylidene)acetamide

A mixture of (Z)-2-(2-bromo-6-fluoro-1-indanylidene) acetamide (5.20 g, 19.25 mmoles) and silver nitrate (10.40 g, 61.18 mmoles, Aldrich) in dimethoxyethane (265 mL) and water (100 mL) was refluxed for 18 hours. The mixture was filtered, and the filtrate was diluted with water (700 mL) and extracted with ethyl acetate (6×100 mL). The combined extracts were washed with water (200 mL) and brine (200 mL), dried over magnesium sulfate, filtered and evaporated in vacuo. The residue was chromatographed on silica gel, eluting with hexane:ethyl acetate (2:1). The fractions containing the compound with Kf=0.50 were combined, evaporated in vacuo, and dried in a vacuum at 80° C. for 18 hours to give 0.50 g (10%) of (Z)-2-(6-fluoro-2-nitrooxy-1-indanylidene)acetamide as a pale orange solid, mp 162°–163° C.; $^1$H-NMR (DMSO-d$_6$): d 7.23–7.71 (m, 5H), 6.93 (d, 1H), 6.72 (s, 1H), 3.54 (dd, 1H, J=6.6 Hz and 18.4 Hz), and 3.29 (d, 1H, J=18.4 Hz); steady-state nOe: irradiation at 6.72 d, observed nOe at 7.41 and 7.71 d.

Anal. Calcd. for $C_{11}H_9FN_2O_4$ (mw 252.20): C, 52.38; H, 3.60; N, 11.11. Found: C, 52.43; H, 3.65; N, 11.03.

EXAMPLE 9

Preparation of (Z)-2-(6-fluoro-2-methoxy-1-indanylidene)acetamide

A mixture of (Z)-2-(2-bromo-6-fluoro-1-indanylidene) acetamide (2.60 g, 9.60 mmoles) and silver nitrate (5.10 g, 27.43 mmoles, Aldrich) in methanol (200 mL) was refluxed for 8 hours. Additional silver nitrate (5.10 g, 27.43 mmoles) was added and the mixture was refluxed for 18 hours. The mixture was filtered, and the filtrate was evaporated in vacuo. The residue was chromatographed on silica gel, eluting with hexane:ethyl acetate (1:4), gradually increasing the polarity to 100% ethyl acetate. The fractions containing the compound with Rf=0.15 with hexane:ethyl acetate (1:1) as the eluant were combined and evaporated in vacuo and dried in a vacuum at 50° C. for 18 hours to give 0.68 g (32%) of crude (Z)-2-(6-fluoro-2-methoxy-1-indanylidene) acetamide as a tan solid. Recrystallization from ethyl acetate:hexane mixtures gave 0.49 g (23%) of (Z)-2-(6-fluoro-2-methoxy-1-indanylidene)acetamide as an off-white solid, mp 128°–130° C.; $^1$H-NMR (DMSO-d$_6$): d 7.13–7.48 (m, 5H), 6.54 (s, 1H), 5.34 (d, 1H), 3.25 (s, 3H), 3.05 (dd, 1H, J=5.7 Hz, 17.3 Hz), and 2.87 (d, 1H, J=17.1 Hz).

Anal. Calcd. for $C_{12}H_{12}FNO_2$ (mw221.225): C, 65.14; H, 5.47; N, 6.33. Found: C, 65.08; H, 5.54; N, 6.26.

EXAMPLE 10

Preparation of (Z)-2-(2-acetoxy-6-fluoro-1-indanylidene)acetamide

A mixture of (Z)-2-(2-bromo-6-fluoro-1-indanylidene) acetamide (0.51 g, 1.90 mmoles), potassium acetate (0.37 g, 3.80 mmoles), and 18-crown-6 (0.06 g, 0.24 mmoles, Aldrich) in acetonitrile (20 mL) and ethanol (10 mL) was sonicated using a Sonicor ultrasonicator for 2 hours, allowing the temperature to rise to 35° C. The mixture was stirred overnight at ambient temperature. Glacial acetic acid (3 mL) was added and the mixture was sonicated for 1.5 hours allowing the temperature to rise to 50° C. The mixture was stirred overnight at ambient temperature and evaporated in vacuo. The residue was dissolved in dichloromethane (100 mL), washed with water (2×50 mL) and evaporated in vacuo. The residue was chromatographed on silica gel eluting with hexane:ethyl acetate (3:1) gradually increasing the polarity to 100% ethyl acetate. The fractions containing the compound with Rf=0.3 in hexane:ethyl acetate (1:1) were combined and evaporated in vacuo to give a solid which was washed with hexane and dried in a vacuum at 50° C. for 18 hours to give 0.22 g (46%) of (Z)-2-(2-acetoxy-6-fluoro-1-indanylidene)acetamide as a white solid, mp 202°–203° C.; $^1$H-NMR (DMSO-d$_6$): d 7.49 and 7.08 (d, 2H), 7.19–7.38 (m, 3H), 6.57 (s, 1H), 6.42 (d, 1H), 3.39 (dd, 1H, J=6.9 Hz, 17.7 Hz), and 2.82 (d, 1H, J=18.0 Hz), 1.91 (s, 3H); steady-state nOe: irradiation at 6.57 d, observed 22% nOe at 7.35 d.

Anal. Calcd. for $C_{13}H_{12}FNO_3$ (mw 249.24): C, 62.64; H, 4.85; N, 5.62. Found: C, 62.75; H, 4.85; N, 5.66.

EXAMPLE 11

Preparation of (E)-2-(6-Fluoro-2-hydroxy-1-indanylidene)acetamide

A solution of (Z)-2-(6-fluoro-2-hydroxy-1-indanylidene) acetamide (5.456 g, 0.026 mol) in dichloromethane:methanol/9:1 (1000 ml) was irradiated by an Canrad-Hanovia quartz, mecury-vapor photochemical immersion lamp, 450 wattts (Ace Glass, 7825–35) for 1h. The volitiles were removed by spin evaporation in vacuo to give a light brown solid residue. This residue was chromatographed on Silica Gel 60 using a step gradient going from ethyl acetate:hexanes/1:1 to ethyl acetate:ethanol/1:1. Fractions containing (E)-2-(6-fluoro-2-hydroxy-1-indanylidene) acetamide were combined and concentrated by spin evaporation in vacuo. The resulting residue was recrystallized from ethanol-hexanes to give 1.31 g (24%) of (E)-2-(6-fluoro-2-hydroxy-1-indanylidene)acetamide as an off-white crystalline solid, m.p., 159°–163° C., NMR(DMSO-d$_6$): d 8.56 (dd, 1H, $J_{HF}$=11.0 Hz, $J_{HH}$=2.9 Hz), 7.67 (br s, 1H), 7.34–7.30 (m, 1H), 7.2–7.13 (m, 1H), 7.06 (br s, 1H), 6.18 (s, 1H), 5.69 (d, 1H, J=6.8 Hz), 4.74 (q, 1H, J=12.1 Hz, J=6.0 Hz), 3.21–3.13 (m, 1H) 2.73–2.66(m, 1H); steady state nOe: irradiation at d6.19, observed 5.4% nOe at d4.74, 4.3% at d7.67 and 1.5% at d 5.69.

Anal. Calcd. for $C_{11}H_{10}FNO_2$ 0.5 $H_2O$ (mw 216.212): C, 61.11; H, 5.13; N, 6.48. Found: C, 61.20; H, 5.17; N, 6.44.

EXAMPLE 12

Preparation of (E)-2-(6-Chloro-1-indanylidene)-N-methylacetamide a) Preparation of 2-Chloro-N-methylacetamide Chloroacetyl chloride (45 g, 398 mmoles, Aldrich) was added dropwise to aqueous methylamine (40%, 30.7 g, 1.31 mol) in 300 ml of water originally at −20° C. with stirring. The temperature of the reaction was raised to 0° C. and stirring was continued until the reaction was no longer exothermic. The resulting solution was acidified with concentrated hydrochloric acid (7 ml) and extracted with dichloromethane (4×250 ml). The organic layer was washed with H$_2$O (250 ml) and spin evaporated in vacuo to give a clear liquid residue. This residue was diluted with pentane (300 ml) and spin evaporated in vacuo to give 15.62 g (37%) of 2-chloro-N-methylacetamide as a white solid; NMR (DMSO-d$_6$): d 8.13 (br s, 1H, NH), 4.02 (s, 2H, CH$_2$), 2.60 (d, 3H, J=4.69 Hz, CH$_3$)

EXAMPLE 13

Preparation of (E)-N-cyclopropyl-2-(1-indanylidene)acetamide a) Preparation of Diethyl((cyclopropylcarbamoyl)methyl) phosphonate 2-Chloro-N-cyclopropylacetamide (20 g, 0.15 moles) was added in portions with stirring to triethyl phosphite (28 g, 0.17 moles, Aldrich) at 110° C. The solution was then heated to 155° C. for 30 minutes, cooled to 125° C., and the volatiles were removed by distillation under aspirator vacuum (15 mm Hg) at this temperature. The residual oil was stirred with pentane (200 mL) while cooling in an ice bath to induce crystallization. Filtration gave 5.2 g (14%) of diethyl((cyclopropylcarbamoyl)methyl)phosphonate as white crystals; m.p. 51°–56° C. The liquor was concentrated and cooled to give 25.3 g (71%) of a second crop; m.p. 50°–56° C. Recrystallization from dichloromethane/hexanes gave the analytical sample, m.p. 55°–57° C.

Anal. Calcd. for $C_9H_{18}NO_4P$: C, 45.96; H, 7.71; N, 5.95. Found. C, 45.85; H, 7.76; N, 5.90.

EXAMPLE 14 (REFERENCE EXAMPLE)

Preparation of (E)-N-Ethyl-2-(7-fluoro-1,2,3,4-tetrahydro-1-naphthylidene)acetamide a) Preparation of 2-Chloro-N-ethylacetamide This compound was prepared in an analogous manner to that in Example 12 with the replacement of aqueous methylamine with aqueous ethylamine (70%, 30.7 g, 0.48 mol) in deionized water (100 ml). The dichloromethane layer was washed with deionized water (150 ml), filtered through glass wool and concentrated by spin evaporation in vacuo to give a pale yellow liquid residue. This residue was concentrated with hexanes (200 ml) and dichloromethane (600 ml) to give 16.01 g (59%) of 2-chloro-N-ethylacetamide. The spectra of this compound was consistent with the preoposed structure and the compound was used without further analysis.

b) Preparation of Diethyl ((N-ethylcarbamoyl)methyl) phosphonate

This compound was prepared in an analogous manner to that on Example 13 with the replacement of 2 chloro-N-cyclopropylacetamide with 2-chloro-N-ethylacetamide. Fractional distillation gave 25.06 g (88%) of diethyl (N-ethylcarbamoyl)methyl)-phosphonate; b.p., 135°–147° C. at 0.50 mm Hg. This compound was used without further analysis.

c) Preparation of (E)-N-Ethyl-2-(7-fluoro-1,2,3,4-tetrahydro-1-naphthylidene)acetamide To a stirred suspension of NaH (80% dispersion in mineral oil, 0.91 g. 0.030 mol, Aldrich) in dimethyl sulfoxide (150 ml) at room temperature under a nitrogen atmosphere was added a solution of diethyl (N-ethylcarbamoyl)methyl) phosphonate (6.8 g. 0.030 mol) in dimethyl sulfoxide (50 ml). The reaction was slightly exothermic. The reaction was stirred for 0.75 h. A solution of 7-fluoro-1-tetralone (5.00 g, 0.030 mol) in dimethyl sulfoxide (60 ml) was added and the reaction was stirred for 1 h. The reaction was poured into ice-cold water (300 ml) and extracted with diethyl ether (3×250 ml). The combined ether phases were washed with water (100 ml) and concentrated by spin evaporation in vacuo to give a golden yellow syrup. This residue was chromatographed on Silica Gel 60 using a step gradient going from ethyl acetate-hexanes/1;3 to ethyl acetate-hexanes 1:1. Fractions containing (E)-N-Ethyl-2-(7-fluoro-1,2,3,4-tetrahydro-1-naphthylidene)acetamide were combined and spin evaporated in vacuo to give 3.74 g of a white solid. Recrystallization from dichloromethane-hexanes gave 3.28 g (46%) of (E)-N-ethyl-2-(7-fluoro-1,2,3,4-tetrahydro-1-naphthylidene)acetamide as a fluffy white solid; m.p., 897°–89° C.

Anal. Calcd. for $C_{14}H_{16}FNO$ (mw 233.278): C, 72.08; H, 6.91; N, 6.00. Found: C,72.05; H, 6.91;N,6.05.

EXAMPLE 15 (REFERENCE EXAMPLE)

Preparation of (E)-N-Ethyl-2-(7-fluoro-1,2,3,4-tetrahydro-1-naphthylidene)acetamide a) Preparation of 2-Chloro-N-ethylacetamide Chloroacetyl chloride (45 g, 398 mmoles, Aldrich) was added dropwise to aqueous ethylamine (70%, 30.7 g, 0.48 mol) in 100 ml of deionised water originally at −20° C. with stirring. The temperature of the reaction was raised to 0° C. and stirring was continued until the reaction was no longer exothermic. The resulting solution was acidified with concentrated hydrochloric acid (7 ml) and extracted with dichloromethane (4×250 mi). The organic layer was washed with deionised H$_2$O (150 ml) filtered through glass wool and concentrated by spin evaporation in vacuo to give a pale yellow liquid residue. This residue was concentrated with hexanes (200 ml) and dichloromethane (600 ml) to give 16.01 g (59%) of 2-chloro-N-ethylacetamide. The spectra of this compound was consistent with the proposed structure and the compound was used without further analysis.

b) Preparation of Diethyl (N-ethylcarbamoyl)methyl) phosphonate

2-Chloro-N-ethylacetamide (15.5 g, 127.5 mmol) was added in portions with stirring to triethyl phosphite (28 g, 0.17 moles, Aldrich) at 110° C. The solution was then heated to 155° C. for 30 minutes, cooled to 125° C., and the volatiles were removed by distillation under aspirator vacuum (15 mm Hg) at this temperature. Fractional distillation gave 25.06 g (88%) of diethyl ((N-ethylcarbamoyl) methyl) phosphonate; b.p., 135°–147° C. at 0.50 mm Hg. This compound was used without further analysis.

c) Preparation of (E)-N-Ethyl-2-(7-fluoro-1,2,3,4-tetrahydro-1-naphthylidene) acetamide To a stirred suspension of NaH (80% dispersion in mineral oil, 0.91 g, 0.030 mol, Aldrich) in dimethyl sulfoxide (150 ml) at room temperature under a nitrogen atmosphere was added a solution of diethyl ((N-ethylcarbamoyl)methyl phosphonate (6.8 g, 0.030 mol) in dimethyl sulfoxide (50 ml). The reaction was slightly exothermic. The reaction was stirred for 0.75h. A solution of 7-fluoro-1-tetralone (5.00 g, 0.030 mol) in dimethyl sulfoxide (50 ml) was added and the reaction was stirred for 1 h. The reaction was poured into ice-cold water (300 ml) and extracted with diethyl ether (3×250 ml). The combined ether phases were washed with water (100 ml) and concentrated by spin evaporation in vacuo to give a golden yellow syrup. This residue was chromatographed on Silica Gel 60 using a step gradient going from ethyl acetate-hexanes/1:3 to ethyl acetate-hexanes/1:1. Fractions containing (E)-N-Ethyl-2-(7-fluoro-1,2,3,4-tetrahydro-1-naphthylidene acetamide were combined and spin evaporated in vacuo to give 3.74 g of a white solid. Recrystallization from dichloromethane-hexanes gave 3.28 g (46%) of (E)-N-ethyl-2-(7-fluoro-1,2,3,4-tetrahydro-1-naphthylidene) acetamide as a fluffy white solid; m.p., 87°–89° C.

Anal. Calcd. for $C_{14}H_{16}FNO$ (mw 233.278): C,72.08; H, 6.91; N, 6.00 Found: C,72.05; H, 6.91; N, 6.05

EXAMPLE 16

Preparation of (Z)-N-Ethyl-2-(7-fluoro-1,2,3,4-tetrahydro-1-naphthylidene)acetamide Fractions from the chromatographic purification described in Example 15 that contained (Z)-N-ethyl-2-(7-fluoro-1,2,3,4-tetrahydro-1-naphthylidene)acetamide were combined and concentrated in vacuo to give 1.07 g (20%) of (Z)-N-ethyl-2-(7-fluoro-1,2,3,4-tetrahydro-1-naphthylidene)acetamide as a white solid; m.p., 117°–118° C.

Anal. Calcd. for $C_{14}H_{16}FNO$ (mw 233.278): C, 72.08; H, 6.91; N, 6.00. Found: C, 71.99; H, 6.89; N,6.01

EXAMPLE 17 (REFERENCE EXAMPLE)

Preparation of (E)-2-(6-Fluoro-1-indanylidene) thioacetamide

A mixture of (E)-2-(6-fluoro-1-indanylidene)acetamide (5.01 g, 26.1 mmol) and 2,4-bis(4-methoxyphenyl)-1,3-dithia-2,3-diphosphetane-2,4-disulfied (Lawesson's Reagent, 5.3 g, 13.1 mmol, Aldrich) in anhydrous toluene (60 ml) was stirred for 18 hrs at room temperature. Additional 2,4-bis(4-methoxyphenyl)-1,2-dithia-2,4-diphosphetane-2,4-disulfied (5.3 g, 13.1 mmol) was added and stirring was continued for 24 hrs. The mixture was heated with a 55° C. water bath and stirred for approximately 3 hrs. The volatiles were removed by spin evaporation in vacuo with the addition of dichloromethane (2×1250 ml). Chromatography of the residual solid on Silica Gel 60 with ethyl ether and dichloromethane followed by chromatography of the pooled fractions containing the product on Silica gel 60 with ethyl acetate and hexanes gave 4.51 g of a yellow solid residue, after removal of the volatiles. The residue was slurried in 300 ml of a solution of ethyl ether and dichloromethane (1:50). Filtration gave 0.945 g (17.4%) of (E)-2-(6-fluoro-1-indanylidene)thioacetamide as a yellow solid: m.p. 178°–179° C.

EXAMPLE 18

Preparation of (E)-N-Cyclopropyl-2-(7-fluoro-1,2,3,4-tetrahydro-1-naphthylidene)acetamide a) Preparation of 3-(4-fluorobenzoyl)propionic acid A mixture of fluorobenzene (104.4 g, 1.09 mol, Aldrich) and succinic anhydride (93.5 g, 0.93 mol) in 1,2-dichlorobenzene (530 mL) was heated to 50° C. Aluminum chloride (245 g, 1.84 mol) was added portionwise keeping the temperature below 60° C. After 4 h at 60° C. followed by 5 h at 80° C., the reaction mixture was poured into a mixture of concentrated HCl (200 mL) and ice water (2 L). The organic layer was separated and the aqueous phase was extracted with dichloromethane. The combined organic phase was dried and concentrated in vacuo. The residue was poured into hexane (2 L) and the resulting solid was filtered and washed with pentane to give 164.1 g (89%) of 3-(4-fluorobenzoyl)propionic acid as a white solid. m.p., 102°–104.5° C. (lit J. Org. Chem. 26, 2667, 1961; m.p., 102.5°–103.5° C.)

b) Preparation of 4-(4-fluorophenyl)butyric acid

A mixture of 3-(4-fluorobenzoyl)propanoic acid (42.3 g, 0.22 mol) and 10% Palladium on carbon (3 g) in acetic acid (250 mL) was hydrogenated at 50 psi and 25° C. for 6 h. The mixture was filtered and concentrated in vacuo. The residue was distilled at 0.02 mm Hg and the product crystallized to give 4-(4-fluorophenyl)butyric acid as a white solid (97%). m.p., 44°–46.2° C. (lit. J. Chem. Soc. 89, 386, 1967; m.p., 45.5°–46.5° C.).

c) Preparation of 7-Fluoro-1-tetralone

A mixture of 4-(4-fluorophenyl)butyric acid (68.2 g, 0.37 mol) and thionyl chloride (155 g, 1.3 mol) was refluxed for 1.25 h. The mixture was concentrated in vacuo to give 75.3 g (100%) of 4-(4-fluorophenyl)butyryl chloride)

To a mixture of aluminum chloride (66 g, 0.50 mol) in carbon disulfide (600 mL) was added dropwise a solution of 4-(4-fluorophenyl)butyryl chloride (75.3 g, 0.37 mole) in carbon disulfide (260 mL) keeping the internal temperature below 10° C. After refluxing for 0.5 h, the reaction mixture was poured into a mixture of concentrated HCl (50 mL) and ice water (800 mL). The mixture was filtered and extracted with diethyl ether. The diethyl ether extracts were dried and concentrated in vacuo to give crude 7-fluoro-1-tetralone. Vacuum distillation gave pure 7-fluoro-1-tetralone b.p., 83° C. at 0.3 mm Hg which solidified to a white solid (94%). m.p., 62°–64° C. (lit, J. Am. Chem. Soc., 89, 386, 1967; m.p., 63.5°–65.0° C.)

d) Preparation of (E)-N-Cyclopropyl-2-(7-fluoro-1,2,3,4-tetrahydro-1-naphthylidene)acetamide This compound was prepared in an analogous manner to Example 27d with the replacement of 6-chloro-1-indanone and diethyl carbamoylmethylphosphonate with 7-fluoro-1-tetralone (7.76 g, 0.05 mol) and diethyl (cyclopropylcarbamoyl)methylphosphonate (11.1 g, 0.05 mol). Chromatography on Silica gel using ethyl acetate:hexanes (1:2) as eluent gave 4.38 g (37%) of (E)-N-Cyclopropyl-2-(7-fluoro-1,2,3,4-tetrahydro-1-naphthylidene)acetamide, m.p., 122.8°–123.3° C.; NMR (DMSO-$d_6$): d 8.00 (d, J=4.0 Hz, 1H), 7.32 (dd, J=11.2 Hz, 1H), 7.04–7.23 (m, 2H), 6.33 (s, 1H), 3.06 (m,2H), 2.69 (m, 3H), 1.70 (m, 2H), 0.66 (m, 2H), 0.40 (m, 2H); steady-state nOe: irradiation at 6.39 d, observed significant nOe at 7.32 d.

Anal. Calcd. for $C_{15}H_{16}FNO$ (mw245.30): C, 73.45; H, 6.57;N, 5.71. Found: C, 73.38; H, 6.64; N, 5.67.

| COMPOUND | Example | M.P. °C. |
|---|---|---|
| (E)-2-(4-Chloro-1-indanylidene)acetamide | 1;k | 196–198 |
| (E)-2-(4-Methyl-1-indanylidene)acetamide | 1;k | 178–180 |
| (E)-1-(2-(6-Fluoro-1-indanylidene)acetyl)pyrrolidine | like 2 | 120–123 |
| (E)-2-(6-Fluoro-1-indanylidene)-N-phenylacetamide | like 2 | 158–161 |
| (E)-1-(2-(6-Fluoro-1-indanylidene)acetyl)azetidine | like 2 | 123–125 |
| (E)-2-(6-Fluoro-1-indanylidene)-N-methoxy-N-methylacetamide | like 2 | 76–78 |
| (Z)-2-(6-Fluoro-2-nitrooxy-1-indanylidene)acetamide | 8 | 162–163 |
| (E)-2-(6-Fluoro-1-indanylidene)-N-(2-hydroxyethyl)acetamide | like 2 | 146–148 |
| (Z)-2-(6-Fluoro-2-methoxy-1-indanylidene)acetamide | 9 | 128–130 |
| (Z)-2-(2,3-Dibromo-6-fluoro-1-indanylidene)acetamide | 6 | 158–163 |
| (E)-2-(6-Fluoro-1-indanylidene)thioacetamide | 14 | 176–179 |
| (E)-N-Cyclopentyl-2-(6-fluoro-1-indanylidene)acetamide | like 2 | 152–154 |
| (Z)-2-(2-Acetoxy-6-fluoro-1-indanylidene)acetamide | 10 | 202–203 |
| (Z)-2-(2-Bromo-6-fluoro-1-indanylidene)acetamide | 5 | 162–163 |
| (E)-2-(4,6-Difluoro-1-indanylidene)-N-(2-hydroxyethyl)acetamide | like 2 | 152–154 |
| (E)-N-Cyclopropyl-2-(7-methyl-1-indanylidene)acetamide | like 2 | 142–144.5 |
| (E)-2-(6-Cyano-1-indanylidene)acetamide | like 1;k | 221–223 |
| (Z)-2-(2-Bromo-4,6-difluoro-1-indanylidene)acetamide | 4 | 187–188 |
| (E)-2-(6-Bromo-1-indanylidene)-N-cyclopropylacetamide | like 2 | 173–174 |
| (E)-2-(6-Bromo-1-indanylidene)-N-methylacetamide | like 2 | 225–227 |
| (E)-2-(6-Methoxy-1-indanylidene)acetamide | like 1;k | 188–192 |
| (E)-2-(7-Chloro-1,2,3,4-tetrahydro-1-naphthylidene)-N-cyclopropylacetamide | like 12c | 170.7–171.8 |
| (E)-2-(5-Bromo-1,2,3,4-tetrahydro-1-naphthylidene)-N-cyclopropylacetamide | like 12c | 178.5–180 |
| (E)-N-(Cyclopropyl-2-(1,2,3,4-tetrahydro-7-methoxy-1-napthylidene)acetamide | like 12c | 128.3–130.6 |
| (E)-N-(Cyclopentyl-2-(7-fluoro-1,2,3,4-tetrahydro-1-naphthylidene)acetamide | like 12c | 166–167 |
| (E)-N-(Cyclopropyl-2-(1,2,3,4-tetrahydro-6-methoxy-1-napthylidene)acetamide | like 12c | 179–180.4 |
| (E)-N-Benzyl-2-(7-fluoro-1,2,3,4-tetrahydro-1-naphthylidene)acetamide | like 12c | 96–98 |
| (E)-N-(Cyclopropyl-2-(5-fluoro-1,2,3,4-tetrahydro-1-naphthylidene)propionamide | like 3;F | 161–162 |
| (E)-2-(7-Fluoro-1,2,3,4-tetrahydro-1-naphthylide)-N-(2-hydroxyethyl)acetamide | like 3;F | 120–122 |
| (E)-2-(6-Fluoro-1,2,3,4-tetrahydro-1-naphthylide)-N-methyl-N-methoxyacetamide | like 3;F | 67–69 |
| (Z)-N-Cyclopropyl-2-(7-fluoro-1,2,3,4-tetrahydro-2,2-dimethyl-1-naphthylidene)acetamide | like 11 | 118–121 |
| (E)-N-Cyclopropyl-2-(7-fluoro-1,2,3,4-tetrahydro-2,2-dimethyl-1-naphthylidene)acetamide | like 11 | 113–115 |
| (E)-2-(7-Fluoro-1,2,3,4-tetrahydro-1-naphthylidene)acetanilide | like 3;F | 119–121 |
| (E)-1-(2-(7-Fluoro-1,2,3,4-tetrahydro-1-naphthylidene)acetyl)azetidine | like 3;F | 58–61 |
| (E)-1-(2-(7-Fluoro-1,2,3,4-tetrahydro-1-naphthylidene)acetyl)pyrrolidine | like 12;c | 141–143 |

-continued

| COMPOUND | Example | M.P. °C. |
|---|---|---|
| (E)-N-(Cyclopropyl-2-(1,2,3,4-tetrahydro-7-methyl-1-napthylidene)acetamide | like 12;c | 151.7–153.9 |
| (E)-N-(Cyclopropyl-2-(1,2,3,4-tetrahydro-5-methoxy-1-napthylidene)acetamide | like 12;c | 156.8–160.3 |
| (Z)-N-cylcopropyl-2-(1,2,3,4-tetrahydro-1-naphthylidene)acetamide | like 13 | 106–113 |
| (E)-2-(6-Chloro-1,2,3,4-tetrahydro-1-naphthylidene)-N-cyclopropylacetamide | like 12;c | 173–174 |
| (Z)-2-(7-Chloro-1,2,3,4-tetrahydro-1-naphthylidene)-N-cyclopropylacetamide | like 13 | 104–105.5 |
| (Z)-N-Cyclopropyl-2-(1,2,3,4-tetrahydro-7-methoxy-1-naphthylidene)acetamide | like 13 | 145–146.1 |
| (Z)-N-Cyclopentyl-2-(7-fluoro-1,2,3,4-tetrahydro-1-naphthylidene)acetamide | like 13 | 147–149 |
| (Z)-2-(7-Fluoro-1,2,3,4-tetrahydro-1-naphthylidene)-N-phenylacetamide | like 13 | 180–184 |
| (E)-2-(6-Chloro-3,4-dihydro-2H-1-benzopyran-4-ylidene)-N-cyclopropylacetamide | like 2 | 171–172 |
| (E)-2-(6-Chloro-3,4-dihydro-2H-1-benzopyran-4-ylidene)-N-methylacetamide | like 2 | 204–205 |
| (E)-2-(6-Chloro-3,4-dihydro-2H-1-benzopyran-4-ylidene)acetamide | like 2 | 168–169 |
| (E)-N-Cyclopropyl-2-(3,4-dihydro-2H-1-benzothiopyran-4-ylidene)acetamide | like 2 | 115–116 |
| (E)-N-2-(3,4-dihydro-2H-1-benzothiopyran-4-ylidene)-N-methylacetamide | like 2 | 91–93 |
| (E)-2-(3,4-dihydro-2H-1-benzothiopyran-4-ylidene)acetamide | like 2 | 175–175 |
| (E)-N-Cyclopropyl-2-(7-fluoro-1,2,3,4-tetrahydro-1-naphthylidene)acetamide | like 18 | 106–111 |

We claim:

1. (E)-2-(4-Chloro-1-indanylidene)acetamide,
(E)-2-(4-Methyl-1-indanylidene)acetamide,
(E)-1-(2-(6-Fluoro-1-indanylidene)acetyl)pyrrolidine,
(E)-2-(6-Fluoro-1-indanylidene)-N-phenylacetamide,
(E)-1-(2-(6-Fluoro-1-indanylidene)acetyl)azetidine,
(E)-2-(6-Fluoro-1-indanylidene)-N-methoxy-N-methylacetamide,
(Z)-2-(6-Fluoro-2-nitrooxy-1-indanylidene)acetamide,
(E)-2-(6-Fluoro-1-indanylidene)-N-(2-hydroxyethyl)acetamide,
(Z)-2-(6-Fluoro-2-methoxy-1-indanylidene)acetamide,
(Z)-2-(2,3-Dibromo-6-fluoro-1-indanylidene)acetamide,
(E)-2-(6-Fluoro-1-indanylidene)thioacetamide,
(E)-N-Cyclopentyl-2-(6-fluoro-1-indanylidene)acetamide,
(Z)-2-(2-Acetoxy-6-fluoro-1-indanylidene)acetamide,
(Z)-2-(2-Bromo-6-fluoro-1-indanylidene)acetamide,
(E)-2-(4,6-Difluoro-1-indanylidene)-N-(2-hydroxyethyl)acetamide,
(E)-N-Cyclopropyl-2-(7-methyl-1-indanylidene)acetamide,
(E)-2-(6-Cyano-1-indanylidene)acetamide,
(Z)-2-(2-Bromo-4,6-difluoro-1-indanylidene)acetamide,
(E)-2-(6-Bromo-1-indanylidene)-N-cyclopropylacetamide,
(E)-2-(6-Bromo-1-indanylidene)-N-methylacetamide,
(E)-2-(6-Methoxy-1-indanylidene)acetamide,
(E)-2-(7-Chloro-1,2,3,4-tetrahydro-1-naphthylidene)-N-cyclopropylacetamide,
(E)-2-(5-Bromo-1,2,3,4-tetrahydro-1-naphthylidene)-N-cyclopropylacetamide,
(E)-N-Cyclopropyl-2-(1,2,3,4-tetrahydro-7-methoxy-1-naphthylidene)acetamide,
(E)-N-Cyclopentyl-2-(7-fluoro-1,2,3,4-tetrahydro-1-naphthylidene)acetamide,
(E)-N-Cyclopropyl-2-(1,2,3,4-tetrahydro-6-methoxy-1-naphthylidene)acetamide,
(E)-N-Benzyl-2-(7-fluoro-1,2,3,4-tetrahydro-1-naphthylidene)acetamide,
(E)-N-Cyclopropyl-2-(5-fluoro-1,2,3,4-tetrahydro-1-naphthylidene)propionamide,
(E)-2-(7-Fluoro-1,2,3,4-tetrahydro-1-naphthylidene)-N-(2-hydroxyethyl)acetamide,
(E)-2-(6-Fluoro-1,2,3,4-tetrahydro-1-naphthylidene)-N-methyl-N-methoxyacetamide,
(Z)-N-Cyclopropyl-2-(7-fluoro-1,2,3,4-tetrahydro-2,2-dimethyl-1-naphthylidene)acetamide,
(E)-N-Cyclopropyl-2-(7-fluoro-1,2,3,4-tetrahydro-2,2-dimethyl-1-naphthylidene)acetamide,
(E)-2-(7-Fluoro-1,2,3,4-tetrahydro-1-naphthylidene)acetanilide,
(E)-1-(2-(7-Fluoro-1,2,3,4-tetrahydro-1-naphthylidene)acetyl)azetidine,
(E)-1-(2-(7-Fluoro-1,2,3,4-tetrahydro-1-naphthylidene)acetyl)pyrrolidine,
(E)-N-Cyclopropyl-2-(1,2,3,4-tetrahydro-7-methyl-1-naphthylidene)acetamide,
(E)-N-Cyclopropyl-2-(1,2,3,4-tetrahydro-5-methoxy-1-naphthylidene)acetamide,
(Z)-N-cyclopropyl-2-(1,2,3,4-tetrahydro-1-naphthylidene)acetamide,
(E)-2-(6-Chloro-1,2,3,4-tetrahydro-1-naphthylidene)-N-cyclopropylacetamide,
(Z)-2-(7-Chloro-1,2,3,4-tetrahydro-1-naphthylidene)-N-cyclopropylacetamide,
(Z)-N-Cyclopropyl-2-(1,2,3,4-tetrahydro-7-methoxy-1-naphthylidene)acetamide,
(Z)-N-Cyclopentyl-2-(7-fluoro-1,2,3,4-tetrahydro-1-naphthylidene)acetamide,
(Z)-2-(7-Fluoro-1,2,3,4-tetrahydro-1-naphthylidene)-N-phenylacetamide,
(E)-2-(6-Chloro-3,4-dihydro-2H-1-benzopyran-4-ylidene)-N-cyclopropylacetamide,
(E)-2-(6-Chloro-3,4-dihydro-2H-1-benzopyran-4-ylidene)-N-methylacetamide,
(E)-2-(6-Chloro-3,4-dihydro-2H-1-benzopyran-4-ylidene)acetamide,
(E)-N-Cyclopropyl-2-(3,4-dihydro-2H-1-benzothiopyran-4-ylidene)acetamide,
(E)-N-2-(3,4-dihydro-2H-1-benzothiopyran-4-ylidene)-N-methylacetamide,
(E)-2-(3,4-dihydro-2H-1-benzothiopyran-4-ylidene)acetamide,
(E)-N-Cyclopropylmethyl-2-(7-fluoro-1,2,3,4-tetrahydro-1-naphthalidene)acetamide, or salt or solvate or ester thereof.

2. A pharmaceutical composition comprising a compound according to claim 1, or pharmaceutically acceptable salt, solvate or ester thereof, together with an acceptable carrier therefor.

3. A method for the treatment of
   a) a condition associated with abnormally raised skeletal muscle tone;
   b) a condition associated with a convulsive state;
   c) anxiety;
   d) pain; or
   e) an inflammatory condition in a mammal, the method comprising administering thereto a therapeutically effective amount of a compound according to claim 1.

* * * * *